(12) United States Patent
McCarthy

(10) Patent No.: US 8,707,954 B2
(45) Date of Patent: Apr. 29, 2014

(54) AIR/OXYGEN SUPPLY SYSTEM AND METHOD

(76) Inventor: Daniel A. McCarthy, Tyler, TX (US)

( * ) Notice: Subject to any disclaimer, the term of this patent is extended or adjusted under 35 U.S.C. 154(b) by 1279 days.

(21) Appl. No.: 12/248,203

(22) Filed: Oct. 9, 2008

(65) Prior Publication Data

US 2010/0094366 A1    Apr. 15, 2010

(51) Int. Cl.
*A62B 7/00*     (2006.01)
*A62B 9/00*     (2006.01)

(52) U.S. Cl.
USPC ............ 128/205.23; 128/204.21; 128/204.18

(58) Field of Classification Search
USPC ............ 128/205.11, 202.22, 204.23, 204.21, 128/200.24, 202.27, 202.28, 204.18, 128/205.23, 205.25, 206.21; 607/3
See application file for complete search history.

(56) References Cited

U.S. PATENT DOCUMENTS

| | | | |
|---|---|---|---|
| 3,613,677 A | 10/1971 | Blasko | |
| 4,196,725 A | 4/1980 | Gunderson | |
| 4,226,234 A | 10/1980 | Gunderson | |
| 4,297,999 A | 11/1981 | Kitrell | |
| 4,693,242 A | 9/1987 | Biard | |
| 4,863,385 A | 9/1989 | Pierce | |
| 5,211,170 A | 5/1993 | Press | |
| 5,398,676 A | 3/1995 | Press et al. | |
| 5,460,174 A | 10/1995 | Chang | |
| 5,651,361 A | 7/1997 | Dearman et al. | |
| 5,738,088 A | 4/1998 | Townsend | |
| 5,810,001 A * | 9/1998 | Genga et al. | 128/202.27 |
| 5,944,013 A * | 8/1999 | Burch | 128/205.14 |
| 5,979,444 A | 11/1999 | Sherrod | |
| 6,213,120 B1 | 4/2001 | Block et al. | |
| 6,378,517 B1 | 4/2002 | Steen | |
| 6,405,728 B1 | 6/2002 | Van Hall et al. | |
| 6,742,399 B2 | 6/2004 | Kunz et al. | |
| 6,895,959 B2 | 5/2005 | Lukas | |
| 6,895,962 B2 | 5/2005 | Kullik et al. | |
| 6,929,006 B2 | 8/2005 | Kruger et al. | |

(Continued)

FOREIGN PATENT DOCUMENTS

| | | |
|---|---|---|
| JP | 11178924 | 6/1999 |
| WO | 2010042677 | 4/2010 |

OTHER PUBLICATIONS

Co-pending U.S. Appl. No. 12/757,815 by Daniel A. McCarthy, filed Apr. 9, 2010.

(Continued)

*Primary Examiner* — Justine Yu
*Assistant Examiner* — Colin W Stuart
(74) *Attorney, Agent, or Firm* — Meyertons, Hood, Kivlin, Kowert & Goetzel, P.C.; Eric B. Meyertons

(57) ABSTRACT

Provided is a method that includes automatically providing air/oxygen at a pre-selected maximum pressure limit, breath volume and respiratory-rate. The pre-selected maximum pressure limit, breath volume, and respiratory-rate are automatically set as a function of a size of a mask coupled to an air/oxygen supply system. Further provided is a ventilator system that includes a ventilator mask, a ventilator supply system, and a mask conduit. The ventilator mask is configured in a size that will fit upon a selected range of sizes of human faces. The ventilator supply system includes an air/oxygen source and an air/oxygen regulator system configured to regulate air/oxygen flow parameters as a function of the size of the mask. The mask conduit is configured to couple the ventilator supply to the ventilator mask.

30 Claims, 6 Drawing Sheets

(56) References Cited

U.S. PATENT DOCUMENTS

| | | |
|---|---|---|
| 7,093,596 B2 | 8/2006 | Muller et al. |
| 7,331,339 B2 | 2/2008 | Smith et al. |
| 7,367,338 B2 | 5/2008 | Baecke et al. |
| 7,497,731 B2 | 3/2009 | Rosenfeldt et al. |
| 7,575,004 B2 | 8/2009 | Weich et al. |
| 7,578,293 B2 | 8/2009 | Matthiessen et al. |
| 7,770,581 B2 | 8/2010 | Balke et al. |
| 2003/0062040 A1 | 4/2003 | Lurie et al. |
| 2003/0165794 A1* | 9/2003 | Matoba .................. 433/114 |
| 2003/0168063 A1* | 9/2003 | Gambone et al. ........ 128/203.16 |
| 2004/0118403 A1 | 6/2004 | O'Connor et al. |
| 2004/0221850 A1 | 11/2004 | Ging et al. |
| 2005/0085799 A1* | 4/2005 | Luria et al. .................. 606/1 |
| 2005/0092324 A1 | 5/2005 | Bowden et al. |
| 2005/0284469 A1 | 12/2005 | Tobia et al. |
| 2006/0278221 A1* | 12/2006 | Schermeier et al. ..... 128/204.18 |
| 2006/0278222 A1 | 12/2006 | Schermeier et al. |
| 2007/0044805 A1 | 3/2007 | Wedler et al. |
| 2008/0000478 A1 | 1/2008 | Matthiessen et al. |
| 2008/0053445 A1 | 3/2008 | Kroupa et al. |
| 2008/0078382 A1* | 4/2008 | LeMahieu et al. ....... 128/200.24 |
| 2008/0078387 A1 | 4/2008 | Vandine |
| 2008/0110464 A1 | 5/2008 | Davidson et al. |
| 2008/0200776 A1 | 8/2008 | Schermeier et al. |
| 2008/0264417 A1 | 10/2008 | Manigel et al. |
| 2009/0020127 A1 | 1/2009 | Boone et al. |
| 2009/0320850 A1 | 12/2009 | Wallnewitz et al. |
| 2010/0147306 A1 | 6/2010 | Townsend et al. |

OTHER PUBLICATIONS

International Search Report and Written Opinion for PCT/US2009/059926 mailed Jun. 22, 2010. (pp. 1-10).
Impact Model 706 Specifications, Sep. 2003.
Impact Uni-Vent 706 from Emergency Medical Products (http://www.buyemp.com/product/1020803.html), Jun. 6, 2008.
International Preliminary Report on Patentability for PCT/US2009/059926 mailed Apr. 21, 2011. (pp. 1-5).
"O-Two Medical Technologies Inc." accessed at <http://www.otwo.com/prod_par.htm>, Jan. 22, 2010. (2 pages).
"CAREvent PAR." Mar. 2008. (2 pages).

\* cited by examiner

AIR/OXYGEN SUPPLY SYSTEM AND METHOD

BACKGROUND

1. Field of the Invention

The present invention generally relates to a system and method for providing air/oxygen to a subject, and more particularly to providing air/oxygen flow from an air/oxygen supply based on the size of a mask coupled to the air/oxygen supply.

2. Description of Related Art

Medical emergencies often call on one or more persons to provide life-saving support. For example, cardiopulmonary resuscitation (CPR) may be performed when a person is not breathing, or breathing inadequately (e.g., during cardiac arrest). CPR generally involves providing air into a person's lungs via the mouth, and performing a series of chest compressions. This may be performed repeatedly to help oxygenate and circulate the blood. Blowing air into the victim's mouth forces air into the lungs to assist respiration and compressing the chest compresses the heart to assist blood circulation. In a situation in which the heart has stopped beating, performing CPR is unlikely to restart the heart, but is intended to maintain a flow of oxygenated blood to the brain and heart, thereby delaying tissue death and extending the opportunity for a successful resuscitation without permanent brain damage. Defibrillation and other advanced life support techniques may also be used to improve the outcome for a victim of cardiac arrest.

CPR techniques can vary depending on the person needing assistance. For example, administering CPR to an adult generally includes providing a set number of full breaths via the mouth, whereas administering CPR to an infant or child may require a larger number of smaller breaths or puffs via the mouth and/or nose. The lower pressure and larger numbers of breaths administered to an infant or child may reduce the likelihood of injury to the respiratory system of the infant or child. Similarly, the number of chest compressions is increased and the force used in administering the chest compressions is reduced when administering CPR to an infant or child. Accordingly, a person who administers CPR must consider several variables and remember a variety of protocols.

CPR is more effective the sooner it is initiated and thus, the time between the onset of the medical emergency and the time of initiating CPR may be critical. Brain cells may begin to die in as little as 4-6 minutes without an adequate supply of oxygen. Unfortunately, medical emergencies can, and often do, happen at locations that are remote to medical facilities and where no trained medical professionals are readily available and, thus, a by-stander may be in the best position to perform CPR.

Although, many people have some form of CPR training, it is believed that a large percentage of the population does not have adequate familiarity with or significant training in CPR and may not be capable of performing CPR properly. As a result, when a medical emergency arises, CPR may be performed incorrectly and can lead to injury of the person in need of help. For example, a by-stander who untrained or inadequately trained, and who attempts to provide CPR to an infant may inadvertently provide full breaths, as opposed to light puffs. As mentioned above, the full breaths may cause damage to the infant's respiratory system. Further, in the stress of an emergency, the chance that a person becomes overwhelmed by this situation and becomes unable to perform CPR correctly and effectively is greatly increased. Also, it is believed that even with training, some people may be unwilling to perform CPR, especially to someone who is not a friend or family member. For example, a by-stander may have fears of becoming infected through bodily contact with a stranger and, as a result, the by-stander may not attempt CPR on the affected person. The lack of a willingness to perform CPR, and/or the inability to perform CPR correctly can seriously jeopardize the health and safety of those in need of assistance. Further, even when performed correctly, the amount of oxygen that can be delivered by mouth-to-mouth breathing may be significantly less than the amount of oxygen needed in an emergency.

SUMMARY

Various embodiments of air/oxygen supply systems and related apparatus, and methods of operating the same are described. In one embodiment, a method includes automatically providing air/oxygen at a pre-selected maximum pressure limit, breath volume and respiratory-rate. The pre-selected maximum pressure limit, breath volume, and respiratory-rate are automatically set as a function of a size of a mask coupled to an air/oxygen supply system.

In another embodiment, a ventilator system includes a ventilator mask and a ventilator supply system. The ventilator mask is configured in a size that will fit upon a selected range of sizes of human faces, and the ventilator supply system includes an air/oxygen source and an air/oxygen regulator system configured to regulate air/oxygen flow parameters as a function of the size of the mask.

In yet another embodiment, a ventilator mask system includes a ventilator mask body and a mask-keying feature. The mask body is configured in a size that will fit upon a selected range of sizes of human faces. The mask-keying feature is indicative of the mask size and is configured to engage a complementary keying feature of a ventilator supply.

In another embodiment, a cardiopulmonary resuscitation (CPR) kit, includes a ventilator mask configured to fit upon a selected range of sizes of human infant faces, a ventilator mask configured to fit upon a selected range of sizes of human child faces, a ventilator mask configured to fit upon a selected range of sizes of human adult faces and a ventilator supply system. The ventilator supply system includes an air/oxygen source and an air/oxygen regulator system configured to regulate air/oxygen flow parameters as a function of the size of the mask.

BRIEF DESCRIPTION OF THE DRAWINGS

Advantages of the present invention will become apparent to those skilled in the art with the benefit of the following detailed description and upon reference to the accompanying drawings in which.

Figure 1:
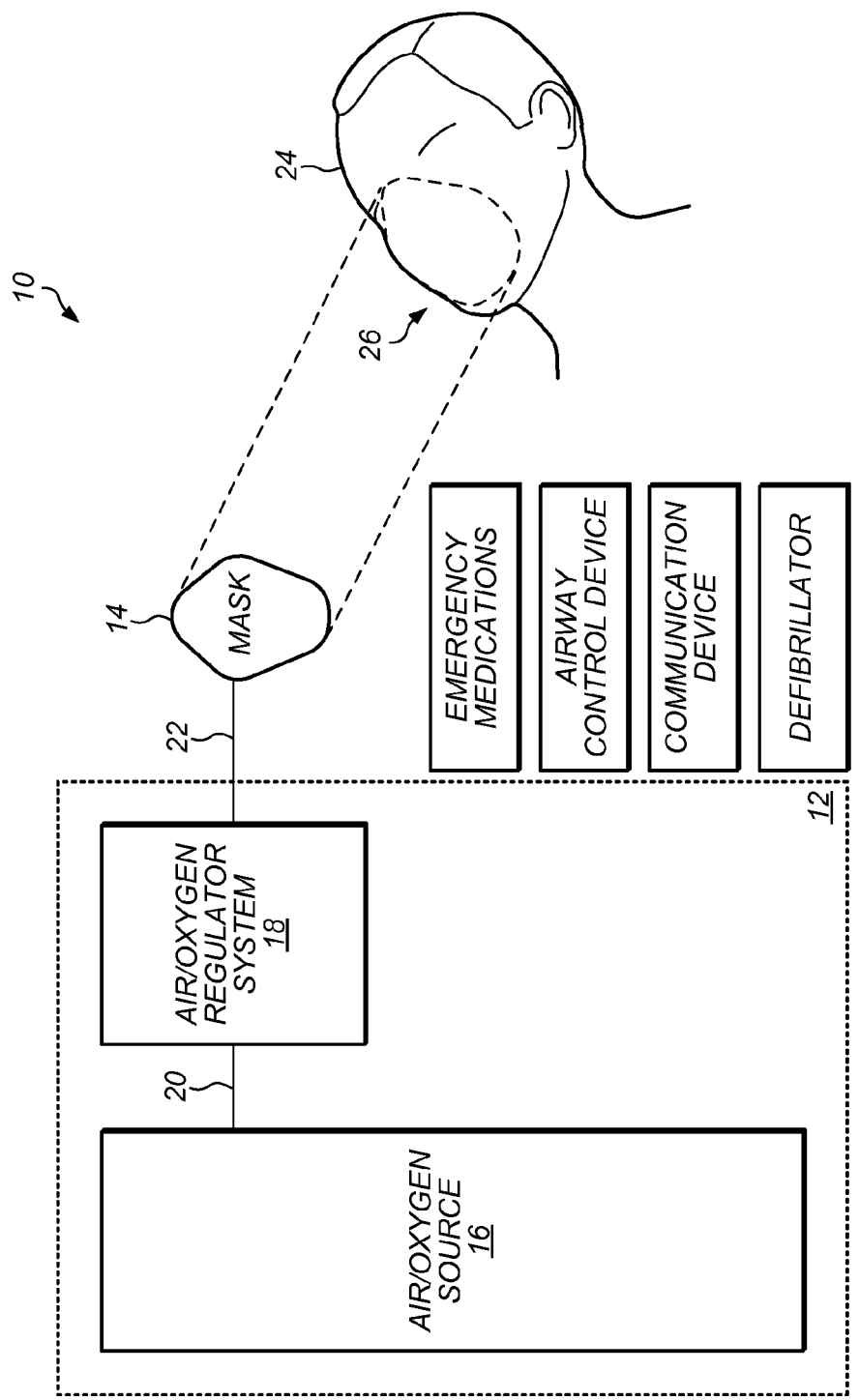
FIG. 1 is a block diagram that illustrates an air/oxygen supply system in accordance with embodiments of the present technique.

While the invention is susceptible to various modifications and alternative forms, specific embodiments thereof are shown by way of example in the drawings and will herein be described in detail. The drawings may not be to scale. It should be understood, however, that the drawings and detailed description thereto are not intended to limit the invention to the particular form disclosed, but to the contrary, the intention is to cover all modifications, equivalents, and alternatives falling within the spirit and scope of the present invention as defined by the appended claims.

DETAILED DESCRIPTION OF ILLUSTRATIVE EMBODIMENTS

As discussed in more detail below, certain embodiments of the present technique include a system and method for automatically providing air and/or oxygen in accordance with a set of preset artificial respiration or ventilation parameters based on the size of the mask used to deliver the air/oxygen. In one embodiment, the method includes providing air/oxygen at a pre-selected pressure (e.g., a maximum pressure limit), breath volume and respiratory-rate as a function of the size of the mask coupled to an air/oxygen supply system. In some embodiments, an air/oxygen system includes a ventilator system having a ventilator mask and a ventilator supply. In one embodiment, the mask that is ultimately coupled to the ventilator supply is chosen from a plurality of mask sizes. The mask sizes include, in some embodiments, an infant sized mask, a child sized mask and an adult sized mask. In certain embodiments, the ventilator system is configured to deliver the air/oxygen in accordance with ventilation parameters associated with the size of the mask that is currently coupled to the supply system of the ventilator. In certain embodiments, the mask includes a mask-keying feature and the ventilator system is configured to assess the size of the mask based on the engagement of the mask-keying feature with a complementary keying feature of the ventilator supply. Such a ventilator may be employed for use in the administration of artificial respiration during CPR. Before discussing embodiments of the present technique in detail, it may be beneficial to discuss embodiments of systems that may be configured to employ such a method and system.

Turning now to FIG. 1, depicted is a block diagram that illustrates a ventilator system 10 in accordance with one or more embodiments of the present technique. The ventilator system 10 includes a ventilator supply system 12 and a ventilator mask 14.

In the illustrated embodiment, the ventilator supply system 12 includes an air/oxygen source ("source") 16, an air/oxygen regulator system ("regulator") 18, a supply conduit 20, and a mask conduit 22. As used herein, "ventilator system" refers to a system configured to mechanically move breathable air and/or oxygen (air/oxygen) into a subject's lungs, to provide artificial respiration for the subject who is not breathing, or breathing insufficiently. Exhalation may occur passively due to normal chest wall recoil. As used herein, "air/oxygen" refers to atmospheric air, medically pure oxygen, or oxygen-enriched air. As used herein, "medically pure oxygen" refers to a gas having an oxygen concentration above approximately 90% by volume. As used herein, "oxygen-enriched air" refers to a gas having an oxygen concentration above that of atmospheric air. As used herein, "subject" refers to a person in need of supplemental air/oxygen and/or cardio pulmonary resuscitation (CPR).

In operation, the ventilator system 10 may be configured to provide a flow of air/oxygen to a subject 24. For instance, the ventilator system 10 may be employed to provide air/oxygen to a subject 24 during CPR. In other words, instead of providing artificial respiration by mouth-to-mouth breathing, physically blowing air/oxygen into the subject's mouth or by some other non-controlled technique, such as a squeezable resuscitation bag, the ventilator system 10 can be employed as the source of the air/oxygen administered to the subject 24 during CPR. In one such embodiment, the mask 14 is placed over a face region 26 of the subject 24, and the ventilator system 10 is operated to deliver air/oxygen from the source 16 to the subject 24 via the supply conduit 20, the regulator 18, the mask conduit 22, and the mask 14.

In certain embodiments, the source 16 is capable of providing pressurized air/oxygen for use by the ventilator system 10. As used herein "pressurized air/oxygen" refers to air/oxygen having a pressure that promotes the flow of the air/oxygen from the ventilator system 10 into the lungs of the subject 24. Pressurized air may have a pressure that is above a minimum-pressure threshold, such as 20 centimeters of water ($mmH_2O$) above ambient air pressure.

In one embodiment, the source 16 includes a cylinder containing the pressurized air/oxygen. The pressure of the air/oxygen may be set significantly above the minimum-pressure threshold such that the air/oxygen in the cylinder is maintained above the minimum-pressure threshold as the air/oxygen is expelled from the cylinder and the pressure of the air/oxygen in the source 16 drops as function of the air/oxygen expelled from the cylinder. The source 16 may include a mechanical device, such as a compressor, configured to move and/or pressurize the air/oxygen. Such a mechanical device may be used to pressurize and/or fill a cylinder of the source 16. In one embodiment, the source 16 may include the mechanical device to move the air from the cylinder to the subject.

In another embodiment, the device may receive air/oxygen from the surrounding atmosphere, another source (e.g., an oxygen separation, generation, or enrichment device) or an air/gas cylinder. The device may, for example, compress the air/oxygen to a pressure above the minimum-pressure threshold before expelling it through the ventilator system 10. The ventilator system 10 may be configured such that the air/oxygen is expelled under pressure from the source 16 and is routed to the subject 24 via the supply conduit 20, the regulator 18, the mask conduit 22, and the mask 14.

The supply conduit 20 includes a path that directs the air/oxygen from an outlet of the source 16 to an inlet of the regulator 18. In an embodiment in which the source 16 and the regulator 18 are disposed directly adjacent to one another, the supply conduit 20 may include a channel formed by the outlet of the source 16 and the inlet of the air/oxygen regulator 18. In an embodiment in which the source 16 and the regulator 18 are not disposed directly adjacent to one another and/or a distance exists between the two, the supply conduit 20 may include a tube, pipe, or the like, that extends between the outlet of the source 16 and the inlet of the regulator 18. In one embodiment, the supply conduit 20 includes a flexible tube, such as plastic tubing. In another embodiment, the supply conduit 20 includes a rigid structure mounted between the source 16 and the regulator 18. For instance, in one embodiment, the supply conduit 20 includes a brass coupler that is disposed between the source 16 and the regulator 18. Coupling between the supply conduit 20, the source 16, and/or the regulator 18 can be provided via various forms of mechanical coupling, such as a threaded connection, an interference fit, a detent feature, an adhesive, or a combination thereof.

The source 16 and the regulator 18 may be removably coupled to one another and/or the supply conduit 20, in one embodiment. Such a configuration may enable independent replacement, reconditioning, and/or recharging of the source 16 and/or the regulator 18. For instance, in an embodiment in which the source 16 includes a cylinder that is empty or low (e.g., having an air/oxygen pressure below a minimum threshold pressure), the cylinder can be disconnected from the regulator 18, recharged with pressurized air/oxygen and reconnected to the regulator 18. In embodiments wherein the source 16 includes an oxygen enrichment and/or separation device, the source 16 can be disconnected and serviced.

The regulator 18 may be configured to regulate the air/oxygen flow from the source 16. In one embodiment, the regulator 18 includes one or more valves that impede the flow of the air/oxygen from the supply conduit 20 and the source 16. By impeding the flow of the air/oxygen, the valve enables the regulator 18 to regulate one or more flow or respiratory parameters of the air/oxygen. As used herein "flow parameters" or "respiratory parameters" refers to characteristics of gas or fluid flow including, but not limited to, pressure, "tidal" or "breath" volume, and breath frequency or rate. As used herein "pressure" may refer to the maximum airway pressure (e.g., maximum pressure limit). The "maximum pressure limit" refers to the maximum pressure to which the subject receiving artificial respiration is exposed. As used herein, the "tidal volume" or "breath volume" refers to the volume of air inspired during each normal cycle. As used herein, "respiratory-rate" refers to the number of breaths over a period of time (e.g., breaths per minute). The breath volume and the respiratory rate may define a flow-rate that is approximately equal to the breath volume multiplied by the respiratory rate. Further, in an embodiment in which a cyclic air/flow is desired, the flow parameters may include an inspiratory time and an expiratory time. As used herein "inspiratory time" refers to time over which the tidal or breath volume is delivered, and "expiratory time" is the time between the end of one inspiratory cycle and beginning of the next inspiratory cycle.

In certain embodiments, the flow parameters may be indicative of the operation of the ventilator system 10. For example, the pressure of the air/oxygen contained by and/or expelled from the source 16 may be indicative of a failed or deficient supply of air/oxygen. In one embodiment, a drop in the air/oxygen pressure below a minimum threshold pressure indicates that the source 16 (e.g., the cylinder) needs to be replaced, recharged, or otherwise serviced.

During a ventilation cycle, the pressure in the airway may increase as air/oxygen is forced into the airway/lungs during an inspiratory/inhalation phase. During artificial respirations, it may be desired that the pressure in the airway remain low. Excess pressure can lead to trauma to the lungs and airway, increase gastric distention, or may be indicative of a blocked airway. Typically adults can tolerate higher peak airway pressures that infants and children. A pressure relief valve may vent pressure above the maximum pressure limit. In such an embodiment, the pressure at which the relief valve opens may vary from infant to child to adult. Further, excess flow beyond what is needed for proper ventilation function during artificial respiration may be expelled from the system via leakage around the mask 14, or shunting through a pressure relief valve. In one embodiment, a relief valve may be integral to the regulator 18 and/or the mask 24, and may open as a function of a maximum pressure limit. In one embodiment, the air/oxygen flow may be configured at a minimum level for the subject 24. Such a configuration may reduce the amount of air/oxygen that is leaked or expelled. In a system that includes a finite amount of air/oxygen in the source 16, the reduced amount of air leaked or expelled may increase the duration of functioning of the ventilator supply system 10.

In certain embodiments, the regulator 18 includes a gauge that provides an indication of the air/oxygen pressure of the gas or fluid housed in the source 16, and/or the flow parameters of the air/oxygen contained by or being expelled from the regulator 18 and/or being delivered through the mask 14. In one embodiment, the current air/oxygen pressure, is indicated by the gauge disposed on and/or integral to the pressure regulator 18. Other indicators can be provided in certain embodiments. For example, in one embodiment, a gauge is provided in coordination with a signal and/or alarm. The signal and/or alarm may be capable of alerting a user or other monitor, such as a person or system conducting maintenance, that the ventilator system 10 is in need of service or repair. The signal and/or alarm may include visible markings, one or more lights, a buzzer, a siren, or the like. For instance, in one embodiment, the gauge may be indicative of the current pressure in the source 16 and have markings indicative of a high pressure, a safe pressure, and/or a low pressure.

Similarly, the pressure of the air/oxygen being delivered to the subject 24 may be indicative of the status of the air/oxygen being administered (e.g., the status of one or more observed flow parameters). In other words, the pressure may indicate whether the path of the air/oxygen is blocked or leaking. For example, an increase in the air/oxygen pressure downstream of the regulator 18 may indicate that the air passage of the subject 24 is blocked (e.g., something is lodged in the subject's throat). Similarly, a drop in the pressure below a certain level may indicate that the mask 14 is not properly secured to the face region 26 of the subject 24, or that a leak is present elsewhere in the ventilation system 10. Accordingly, in some embodiments the gauge may be used in coordination with a signal and/or alarm. The signal and/or alarm may provide an indication to a user that the ventilator system 10 is functioning properly or not. The signal and/or alarm may include visible markings on the gauge, one or more lights, a buzzer, a siren, or the like. For instance, in one embodiment, the gauge may have markings indicative of a high pressure (blockage), a safe pressure (proper flow), and/or a low pressure (leakage). In one embodiment, the pressure assessed by the gauge may be used to trigger the signal and/or alarms based on the status of the air/oxygen being administered.

In certain embodiments, the regulator 18 includes a manual valve. For instance, the regulator 18 may include a valve having a lever, knob, dial, button, or the like that is actuated by a user. Actuation of the manual valve may operate the valve to increase or decrease one or more flow parameters of air/oxygen. Thus, a user can manually adjust the valve of the regulator 18 to set one or more flow parameters of the ventilator system 10. In another embodiment, the regulator 18 may include an automatic valve configured to regulate the flow parameters. The automatic valve may enable adjustments of the flow parameters of the ventilator system 10 without a significant manual intervention. For example, in one embodiment, the system 10 may include a processor (e.g., an electrical circuit or mechanical circuit) configured to receive an input that is indicative of desired flow parameters. The processor may provide an output configured to operate the valve to maintain flow of the air/oxygen at or near the desired flow parameters. For instance, where a breath volume, maximum pressure limit, and respiratory-rate is desired (e.g., an airflow profile that replicates one or more breathes) the automatic valve may open and close automatically to provide flow of air/oxygen to the subject 24 at the desired breath volume, maximum pressure limit, and respiratory-rate.

The mask conduit 22 includes a path that routes air/oxygen from an outlet of the ventilator supply system 12 to an inlet of the mask 14. In an embodiment in which the ventilator supply system 12 and the mask 14 are disposed directly adjacent to one another, the mask conduit 22 may include the channel formed by the outlet of the ventilator supply system 12 and the inlet of the mask 14. In an embodiment in which the ventilator supply system 12 and the mask 14 are not disposed directly adjacent to one another and/or a substantial distance exists between the two, the mask conduit 22 may include a tube, pipe, or the like, that extends between the outlet of the ventilator supply system 12 and the inlet of the mask 14. For example, the mask conduit 22 may include a length of conduit extending from an outlet of the air/oxygen regulator 18 to a collar of the mask 14. In one embodiment, the mask conduit 22 includes a flexible tube, such as plastic tubing. In another embodiment, the mask conduit 22 includes a rigid component spanning the distance between the outlet of the ventilator supply system 12 and the inlet of the mask 14.

In some embodiments, the ventilator supply system 12 and the mask 14 may be removably coupled to one another and/or the mask conduit 22. Coupling between the mask conduit 22, the ventilator supply 12, and/or the mask 14 may be provided in various manners. In one embodiment, the connections include a threaded connection, an interference fit, locking detent features, an adhesive, or a combination thereof. Such a configuration may simplify the exchange of system components, such as the exchange of one mask 14 for another. For example, where the mask 14 is no longer suitable for service (e.g., the mask has a leak) or does not fit well onto the face region 26 of the subject 24, the interchangeable nature of the mask 14 may enable a user to remove the mask 14 and replace it with another mask.

In some embodiments, the mask conduit 22 and the mask 14 are integral with one another. For example, the mask 14 may include a hollow protrusion that extends from the mask 14 (e.g., a collar) that defines an inlet of the mask 14. The end of the collar opposite the mask 14 may be configured to mate with a complementary feature of the outlet of the ventilator system 12. Thus, at least a substantial portion of the mask conduit 22 is formed from the collar of the mask 14. In such an embodiment, the collar may enable coupling of a tube, connector, or other conduit to the mask 14. Further, the collar may provide an initial point of entry into the mask 14 for the air/oxygen and may route the air/oxygen from the inlet of the mask 14 into the concave region of the mask 14.

The interface between the mask 14 and the supply system 12 may include one or more keying features. In such an embodiment, the keying features may ensure that the mask 14 is installed in correct orientation relative to the supply system 12, that only certain mask 14 may be used in conjunction with the supply system 10, and/or may be used to assess the type and/or size of a mask 14 coupled to the ventilator supply 12. Also, a keying feature between the supply system 12 and the mask 14 could be required to allow air/oxygen flow through the system. This would ensure that the mask 14 is appropriately connected to the supply system 12 in order for air/oxygen flow to commence. In other words, without proper connection of the mask 14, and/or keying feature activation, air oxygen flow cannot begin. As discussed in more detail below, settings of the ventilator system 10 may be configured based on the size of the mask 14 determined by the assessment.

The mask 14 generally includes a device that routes air from the ventilator system 10 to the respiratory system of the subject 24. During use, the mask 14 may be placed over the face region 26 and held in place by a user. The user may press the mask 14 towards the face region 26 to promote a seal between mask 14 and the face region 26 of the subject 24. In certain embodiments, the mask 14 includes a ventilator mask that is secured to and placed over the face region 26 of the subject 24.

In one embodiment, the mask 14 includes a body having curvatures generally shaped to the subject's face region 26. For example, a body of the mask 14 may be formed from plastic that is molded to fit the contours of one or more types of face shapes. Generally, the mask 14 includes a concave shape that enables fitting the mask 14 over the nose and mouth of the subject 24. In some embodiments, the mask 14 includes rubber bands, elastic straps, or the like that can be disposed around the head and/or ears of the subject 24 and configured to secure the mask 14 to the subject 24 and further promote a seal of the mask 14 to the face region 26. In one embodiment, the mask 14 includes an additional sealing element, such as a foam or plastic ring, disposed along a sealing edge of the mask 14. The sealing element may promote the seal of the mask 14 to the face region 26 of the subject 24. As discussed above with regard to the mask conduit 22, the mask 14 may include a collar. The mask 14 may include a pressure relief valve as discussed previously.

In one embodiment, the mask 14 or another portion of the system 10 may include an exhalation port. The exhalation port may include a one-way valve that closes with the forward flow of air/oxygen during inspiration and opens as the air/oxygen moves in the opposite direction during the expiratory phase to expel expired air into the environment. The natural recoil of the chest walls generally provides the force to expel air during the expiratory phase.

In certain embodiments, the mask 14 may be configured in a size that will fit upon a selected range of sizes of human faces. The size of the mask 14 may affect how the mask secures and seals against the face region 26 of the subject 24. For example, if the mask 14 is too small, the sealing edge of the mask 14 may rest on the nose of the subject 24 and fail to provide an effective seal against other portions of the face, thereby allowing the air/oxygen to leak around the mask 14, as opposed to the air/oxygen being delivered to the lungs of the subject 24. If the mask 14 is too large, the sealing edge of the mask 14 may extend over the cheeks and chin of the subject 24, once again failing to provide an effective seal. However, where the mask 14 is fit properly to the face region 26 of the subject 24, the sealing edge of the mask 14 may provide an effective seal with the face region 26, thereby enabling the mask 14 to hold a sufficient pressure to route the air/oxygen into the lungs of the subject 24.

In some embodiments, the different sized mask 14 may be available to cover multiple size ranges of subjects 24. Each of these ranges may account for various shapes and sizes of faces. For example, in one embodiment, an adult-sized mask 14 is configured to fit a range of adult or large sized face regions 26, a child-sized mask 14 is configured to fit a range of child or medium sized face regions 26, and an infant-sized mask 14 is configured to fit a range of infant or small sized face regions 26. Thus, when operating the ventilator system 10, a user can assess the size of the subject 24 and/or the size of the face region 26 of the subject 24, select the mask 14 that appears to provide a sufficient fit and/or seal to the face region 26, couple the appropriate mask 14 to the ventilator supply system 12, secure the mask 14 to the face region 26, and proceed with providing air/oxygen to the subject 24 via the ventilation system 10. A sufficient fit may be assessed by observing whether or not a sealing edge of the mask 14 appears to contact at least a substantial portion of the face region 26, and observing the rise and fall of the subject's chest in relation to the inflow and outflow of air/oxygen as the ventilation supply system cycles.

Operation of the ventilator system 10 may include a series of steps to provide the flow of air/oxygen to the subject 24. For instance, in one embodiment, a user transports the ventilator system 10 to the subject 26, assesses the subjects face region 26, and selects the mask 14 that appears to fit snuggly around the nose and mouth of the subject 24 and that appears to provide a sufficient seal about the face region 26. The user may, then, couple the mask 14 to the ventilator supply system 12, secure the mask 14 to the face region 26 of the subject 24 and operate the ventilator system 10. Operating the ventilator system 10 may include setting the flow parameters, such as the maximum pressure limit, breath volume, and respiratory-rate of the air/oxygen. In an embodiment in which the ventilator system 10 is pre-configured to provide air/flow in accordance with a single set of flow parameters, however, the ventilator system 10 may not be conducive to use with a subject 26 requiring a different set of flow parameters. For example, where the ventilator system 10 is pre-configured to operate at a maximum pressure limit, breath volume and respiratory-rate, suitable for an adult, the ventilator system 10 may not be useful for administering artificial respiration to an infant. Further, even where a plurality of pre-determined flow parameters are available for the user to choose from, the user may not select the proper flow-parameters. For instance, the user may not know which settings to use, or the user may select the incorrect setting inadvertently. Such a mistake could result in injury to the subject 24, or may result in insufficient or excessive air/oxygen pressure, breath volume and respiratory-rate delivered to the subject 24. As discussed in more detail below, certain embodiments include a system and method for automatically providing air/oxygen at pre-selected flow parameters (e.g., maximum pressure limit, breath volume, and respiratory-rate) as a function of the characteristics (e.g., the size) of the mask 14 coupled to the ventilator supply system 10.

Figure 2:
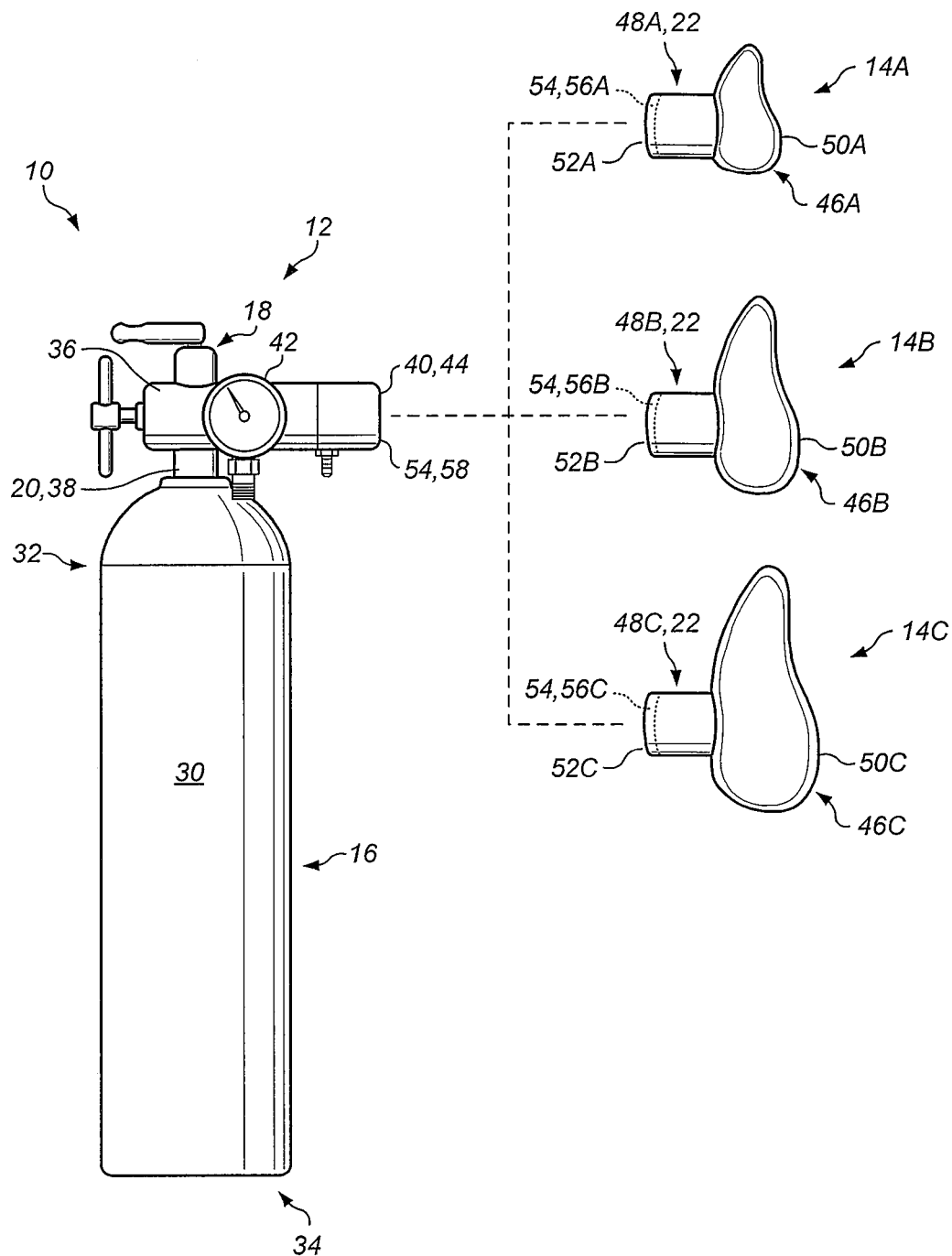
FIG. 2 is a schematic diagram that illustrates multiple masks having varying sizes that are coupleable to the air/oxygen supply system in accordance with embodiments of the present technique.

FIG. 2 is a schematic diagram that illustrates an embodiment of the ventilator system 10 in accordance with one or more embodiments. As depicted, the ventilator system 10 includes the ventilator supply system 12, and a plurality of masks 14A, 14B, and 14C. The ventilator supply system 12 includes the source 16 and the regulator 18. The source 16 includes a cylinder 30 having a first end 32 and a second end 34. In the illustrated embodiment, the supply conduit 20 includes a rigid structure that is integral with the regulator 18 and threaded into the first end 32 of the cylinder 30. The regulator 18 includes a regulator body 36 having an inlet 38 integrated with the supply conduit 20, and a supply outlet 40 opposite the inlet 38. In the illustrated embodiment, the regulator 18 further includes a gauge 42 coupled to the body 36, and the supply outlet 40 includes a connector 44 that is configured to couple directly to the mask conduit 22. No tubing or additional conduit extends from the supply outlet 40.

In the illustrated embodiment each of the masks 14A, 14B, and 14C comprise a mask body 46A, 46B, and 46C, a mask inlet 48A, 48B, and 48C, and a sealing edge 50A, 50B, and 50C. No tubing or additional conduit extends from the inlets 48A, 48B, and 48C. The inlets 48A, 48B, and 48C each include connectors (e.g., collars) 52A, 52B, and 52C that are configured to couple directly to the connector 44 of the supply outlet 40.

The masks 14A, 14B, and 14C may include various types and/or shapes. In the illustrated embodiment, the body 46A of the first mask 14A has a small size, the body 46B of the second mask 14B has a medium size, and the body 46C of the third mask 14C has a large size. The small size mask 14A may be conducive for use with subjects 24 having smaller face regions 26, such as infants, and thus may be referred to as an infant-sized mask. The medium size mask 14B may be conducive for use with subjects 24 having medium sized face regions 26, such as children, and may be referred to as a child-sized mask. The large size mask 14C may be conducive for use with subjects 24 having larger sized face regions 26, such as adults, and may be referred to as an adult-sized mask. Each of the masks 14A, 14B, and 14C are coupleable to the ventilator supply system 12, as indicated by the dashed line between the connector 44 and each of the collars 52A, 52B, and 52C of the mask 14A, 14B, and 14C. Accordingly, a user may select one of the available masks 14A, 14B, and 14C, couple the selected mask 14A, 14B, or 14C to the ventilator supply system 12, secure the mask 14A, 14B, or 14C to the face region 26, and administer the air/oxygen to the subject 24.

In certain embodiments, the ventilator system 10 is configured to select operational parameters based on characteristics of the mask 14. For example, the ventilator system 10 may be configured to automatically provide air/oxygen in accordance with a pre-selected set of flow parameters based on one more characteristics of the mask 14 coupled to the ventilator supply system 12. In one such embodiment, the ventilator system 10 provides air/oxygen at a pre-selected maximum pressure limit, breath volume, and/or respiratory-rate based on the size of the mask 14 coupled to the ventilator supply system 12. The pre-selected flow parameters may include a predetermined set of flow parameter values that are associated with each size of the mask 14. For example, in an embodiment in which the infant-size mask 14A is coupled to the ventilator supply system 12, the ventilator system 10 may be automatically configured to provide air/oxygen in accordance with one or more pre-selected flow parameters that are appropriate for artificial respiration for an infant. In an embodiment in which the child-size mask 14B is coupled to the ventilator supply system 12, the ventilator system 10 may be automatically configured to provide air/oxygen flow in accordance with one or more pre-selected flow parameters that are appropriate for artificial respiration for a child. In an embodiment in which the adult-size mask 14C is coupled to the ventilator supply system 12, the ventilator system 10 may be automatically configured to provide air/oxygen flow in accordance with one or more pre-selected flow parameters that are appropriate for artificial respiration for an adult. Other embodiments may include any number of sizes and types of mask and/or sets of pre-selected flow parameters. For example, additional sizes and associated flow parameters may be available for males and females. Further, two mask 14 may have the same size, but may be associate with varying flow parameters. For example, one size of mask may be designated as a high-pressure type mask that is associated with pre-selected flow parameters having a higher maximum pressure, or a low-pressure type mask that is associated with pre-selected flow parameters having a lower maximum pressure. Further, multiple mask sizes may be associated with a set of flow parameters. For example, ventilation parameters appropriate for children may be engaged by use of toddler sized mask or a larger child sized mask.

Table 1 provides an exemplary listing of flow parameters for an adult, a child and an infant. The information in this table is derived from recommendations provided by the American Heart Association (AHA). The AHA generally assumes that an infant includes a baby up to one year of age, a child is from one year to eight years of age, and an adult is over eight year of age. The values listed in Table 1 are based on recommendations of the AHA although each value may not be explicitly set forth by the AHA. For example, the AHA does not provide a tidal volume, but instead recommends a tidal volume sufficient for visible chest rise. For the purposes of one embodiment based on observation and clinical experience, the breath volume ($V_T$) of 100 cc for an infant is based on an approximate infant weight of 10 kg and a ratio of 10 cubic centimeters (cc) per kilogram (kg). Similarly, the breath volume of 300 cc for a child is based on an approximate child weight of 30 kg and a ratio of 10 cc/kg. The breath volume for an adult of 600 cc is based on the recommended range of 500-600 cc provided by the AHA. It will be appreciated that these values are exemplary of one embodiment of the system and may be modified based on the application and/or based on revised or other relevant standards, such as those provided by the AHA.

TABLE 1

Flow/Respiratory Parameters

| | Breath Volume ($V_T$) (cc) | Respiratory Rate (RR) (breaths/min) | Peak Pressure $P_{IP}$ (maximum pressure limit) (cmH$_2$0) | I:E Ratio | Flow Rate (L/min) | Mask Size |
|---|---|---|---|---|---|---|
| Adult | 600 | 10 | 40 | 1:5 | 6 | Adult |
| Child | 300 | 20 | 20 | 1:2 | 6 | Child |
| Infant | 100 | 30 | 20 | 1:1 | 3 | Infant |

In accordance with an embodiment based on the parameters listed in Table 1, in one embodiment, the ventilator system 10 is automatically configured to provide air/oxygen having a maximum pressure limit of 20 centimeters of water (cmH$_2$O), a breath volume of 100 cubic centimeters (cc), a respiratory-rate of 30 breaths/minute, an I:E ratio of 1:1, and/or a flow rate of 3 liters per minute (L/min) when the infant-size mask 14A is coupled to the ventilator supply system 12. In one embodiment, the ventilator system 10 is automatically configured to provide air/oxygen having a maximum pressure limit of 20 cmH$_2$O, a breath volume of 300 cc, a respiratory-rate of 20 breaths/min, an I:E ratio of 1:2, and/or a flow rate of 6 L/min, when the child-size mask 14B is coupled to the ventilator supply system 12. In one embodiment the ventilator system 10 is automatically configured to provide air/oxygen having a maximum pressure limit of 40 cmH$_2$O, a breath volume of 600 cc, a respiratory-rate of 10 breaths/min, an I:E ratio of 1:5, and/or a flow rate of 6 L/min when the adult-size mask 14C is coupled to the ventilator supply system 12. The I:E ratio is a ratio of the time of the inspiratory phase to the expiratory phase of the respiratory cycle. The AHA recommends that each breath be given over one second (e.g., on second for the inspiratory phase). For example, based on the adult respiratory parameters of Table 1, the I:E ratio of 1:5 is determined by 10 breaths per minute (e.g., six seconds per breath), where one second is needed for the inspiratory phase and the other five seconds are used for the expiratory phase. In other embodiments, one or more of the pre-selected flow parameters includes a range (e.g., a maximum and minimum value), as opposed to a single target value. Further, in other embodiment, the ventilation technique may be varied. For example, one embodiment may include pressure-controlled ventilation. For example, the inspiratory phase of the breath may be given until a certain pressure is reached, and the expiratory phase may, then, begin.

Further, one embodiment may provide for a low flow of oxygen during the expiratory phase of the respiratory cycle to assist in the dilution and washout of expired carbon dioxide from the mask. This may decrease the re-breathing of carbon dioxide that may remain in the mask from the previously expired breath.

In one embodiment, the connection between the mask 14 and the ventilator supply 12 includes at least one keying feature that is indicative of the size, type and/or other characteristics of the mask 14. In the illustrated embodiment, a keying feature 54 includes a mask-keying feature 56A, 56B, or 56C that is configured to engage a complementary-keying feature 58 of the ventilator supply 12 when the mask 14 is coupled to the ventilator supply 12. Based on the keying feature 54, the ventilator system 12 may be automatically configured to output air/oxygen having flow parameters in accordance with pre-selected flow parameters that are associated with the size, type and/or other characteristics of the mask 14. As depicted in FIG. 2, the keying feature 54 may include mask-keying features 56A, 56B, and 56C integral with the mask inlets 48A, 48B, and 48C, respectively. The complementary-keying feature 58 may be integral with the connector 44 at the outlet 40 of the air/oxygen supply system 12. In other embodiments, the keying feature 54 may include a mask-keying feature 56A, 56B, or 56C located anywhere on the mask 14 and a complementary keying feature located anywhere on the supply system 12.

Figure 3:
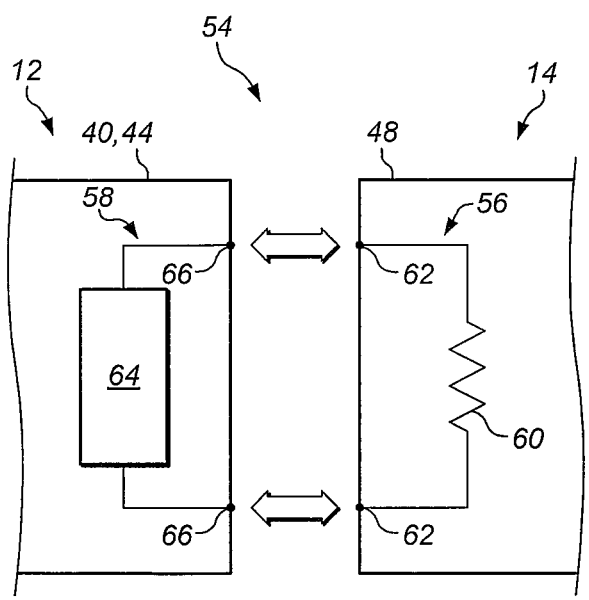
FIG. 3 is a schematic diagram of a keying feature in accordance with embodiments of the present technique.
Figure 4A:
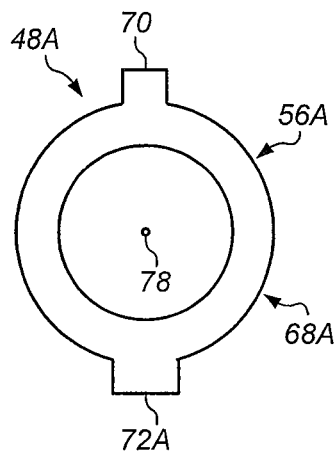
FIG. 4 is a schematic diagram of another keying feature in accordance with embodiments of the present technique.
Figure 4B:
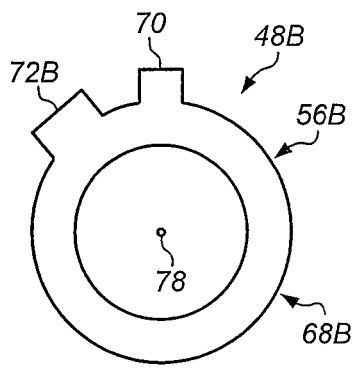
Figure 4C:
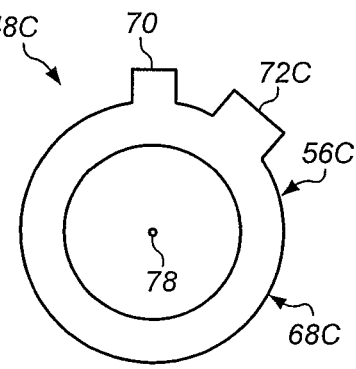
Figure 4D:
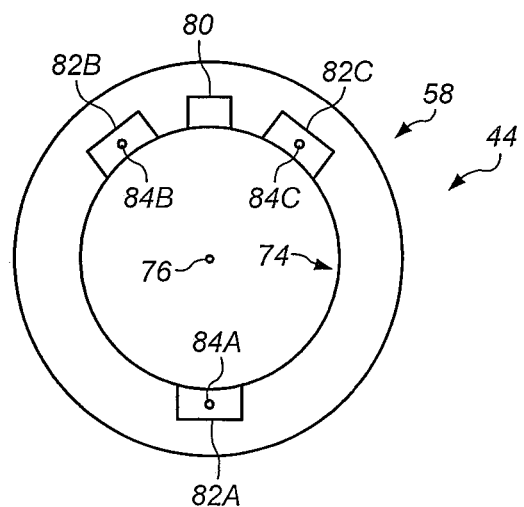

FIG. 3 is a schematic diagram of the keying feature 54 in accordance with one embodiment of the present technique. The illustrated embodiment includes an electrical keying feature. As used herein "electrical keying feature" refers to a keying feature that employs electrical energy to generate, transmit, modify, and/or receive an electrical signal. It is to be understood that a wide variety of electrical coupling features may be used, including software recognition tools. In one embodiment, the system may employ software that is configured to exchange data and/or signals between components of the system 10. For example, in one embodiment, when the mask 14 is coupled to the supply system 12, the mask-keying feature 54 may be configured to exchange data via one or more communication protocols. In one embodiment, the mask-keying feature 56A, 56B or 56C may include a device configured to generate data that is transmitted as one or more signals (e.g., electrical signals) received by a device of the complementary keying feature 58. Such an embodiment may include "handshaking." As used herein, "handshaking" may refer to an automated process of communication used to negotiate parameters that are acceptable to equipment and systems at both ends of a communication channel. In another embodiment, the keying feature 54 may include a magnetic and/or an electromagnetic device. For example, in one embodiment, the mask-keying feature 56A, 56B or 56C may include a magnetic device, e.g., a rare earth magnet or an electromagnetic transmitter/coil, that is configured to generate a magnetic field indicative of the type/size of the mask 14, and the complementary keying feature 58 may include an electromagnetic receiver that is configured to sense the magnetic field for use in assessing and determining the type/size of the mask 14. In yet another embodiment, the keying feature 54 may include a radio-frequency (RF) device. For example, in one embodiment, the mask-keying feature 56A, 56B or 56C may include a radio-frequency transmitter that is configured to generate a radio signal indicative of the type/size of the mask 14, and the complementary keying feature 58 may include radio-frequency receiver that is configured to sense the radio signal for use in assessing and determining the type/size of the mask 14.

In the illustrated embodiment, the mask-keying feature 56 includes a resistor 60 coupled in series with two nodes 62 disposed proximate the inlet 48 of the mask 14. The complementary keying feature 58 includes an electrical circuit 64 coupled to two nodes 66 disposed proximate the connector 44 of the air/oxygen supply 12. In one embodiment, the resistor 60 has a resistance value that is indicative of the type and/or size of the mask 14. For instance, each of the masks 14A, 14B, and 14C may include a resistor 60 that has a different resistance value that is indicative of an infant, a child, or an adult sized mask, respectively. Accordingly, assessing the resistance value of the resistor 60 may indicate the type and/or size of the mask 14. In one embodiment, the resistance value may be indicative of one or more flow parameters and the mask 14 may include a plurality of resistors that are indicative of the flow parameters and one or more modes of operating the ventilator system 10.

In one embodiment, when the inlet 48 of the mask 14 is coupled to the connector 44 of the ventilator supply 12, the nodes 62 and 66 are electrically coupled to one another, thereby completing an electrical path between the terminals of the resistor 60 and the electrical circuit 64. Such a connection may enable the electrical circuit 64 to assess the value of the resistor 60. For instance, the electrical circuit 64 may generate a current across the resistor 60 and assesses the drop in voltage across the resistor 60 to determine a resistance value of the resistor 60. Based on the resistance value of the resistor 60, the ventilator system 10 may be automatically configured to provide air/oxygen flow in accordance with a given set of flow parameters. For instance, in one embodiment, the electrical circuit 64 may transmit a signal to an electrically controlled actuator to adjust the regulator 18 to regulate the flow of air/oxygen to a pre-selected maximum pressure limit, breath volume, and/or respiratory-rate. In such an embodiment, the ventilator system 10 may employ a processor that receives a signal from the electrical circuit 64, interprets the signal, retrieves from a memory one set of a plurality of pre-selected sets of flow parameters that is associated with the resistor value, and transmits one or more signals that are configured to operate the regulator 18 in accordance with the set of pre-selected flow parameters associated with the resistor value.

FIGS. 4A-4D are cross-sectional views that illustrate one or more features of the keying feature 54 in accordance with one or more embodiments of the present technique. The illustrated embodiment includes a mechanical keying feature. As used herein "mechanical keying feature" refers to a keying feature that employs mechanical interfaces between a plurality of structural members. In the illustrated embodiment, the mask-keying features 56A, 56B, and 56C include the inlets 48A, 48B, and 48C of the mask 14 having inlet profiles 68A, 68B, and 68C of varying cross-sections. The connector 44 includes the complementary keying feature 58 having a profile that is configured to accept each of the inlet profiles 68A, 68B, and 68C in a unique orientation relative to the complementary keying feature 58. For instance, the inlet profile 68A of FIG. 4A includes a first protrusion 70 and a second protrusion 72A that extend radially outward from the circumference of the inlet 56A. The first protrusion 70 is located at the twelve-o'clock position and the second protrusion 72A is located at approximately the six-o'clock position (e.g., approximately 180 degrees of angular offset from the first protrusion 70). The inlet profile 68B of FIG. 4B includes a first protrusion 70 and a second protrusion 72B that extend radially-outward from the circumference of the inlet 56B. The first protrusion 70 is located at the twelve-o'clock position and the second protrusion 72B is located at approximately the eleven-o'clock position (e.g., approximately thirty-degrees of angular offset in the counter-clockwise direction from the first protrusion 70). The inlet profile 68C of FIG. 4C includes a first protrusion 70 and a second protrusion 72C that extend radially-outward from the circumference of the inlet 56C. The first protrusion 70 is located at the twelve-o'clock position and the second protrusion 72C is located at approximately the one-o'clock position (e.g., approximately thirty-degrees of angular offset in the clockwise direction from the first protrusion 70).

The complementary keying feature 58 includes a connector profile 74 that is complementary to the protrusions 70, 72A, 72B, and 72C of the profiles 68A, 68B, and 68C such that each of the inlets 56A, 56B, and 56C can be inserted longitudinally into the connector 44 (e.g., along a longitudinal axis 76 that extends through the center of the connector 58 and that aligns with a longitudinal axes 78 of the inlets 56A, 56B, and 56C when the keying features are mated). For instance, the connector profile 74 includes a first indention 80, a second indention 82A, a third indention 82B, and a forth indention 82C that are complementary to the first protrusion 70, and the second protrusions 72A, 72B, and 72C, respectively. The keying feature 54 ensures that each of the inlets 56A, 56B, and 56C can be inserted in only a single orientation relative to the connector 58. Thus, when a mask 14 having a mask-keying feature of a given profile 68A, 68B, or 68C is coupled to and engages the complementary keying feature 58, only one of the second protrusions 72A, 72B, or 72C will extend into only one of the indentations 82A, 82B, or 82C.

The ventilator system 10 may be automatically configured to set the flow parameters based on the protrusion that 72A, 72B, or 72C that engages the complementary keying feature 58. For example, in one embodiment, the second protrusion 72A, 72B, or 72C of the mask-keying feature 56A, 56B, or 56C engages and depresses one of a plurality of stems 84A, 84B, or 84C that extend longitudinally into the second indentations 82A, 82B, or 82C, respectively. The movement of the stem 84A, 84B, or 84C may engage a component of the regulator 18, such as a valve, in a manner that configures the regulator 18 to provide air/oxygen in accordance with a set of flow parameters. The movement of each of the stems 84A, 84B, or 84C may engage the regulator 18 in a different manner (e.g., depressing a ball valve by a varying distance), thereby enabling the ventilator system 10 to provide air/oxygen flow in accordance with one of three pre-selected flow parameters based on the mask 14A, 14B, or 14C coupled to the system 10. Other embodiments may include multiple protrusions engaging the complementary keying feature such that the flow parameters are based on the combination.

Figure 5:
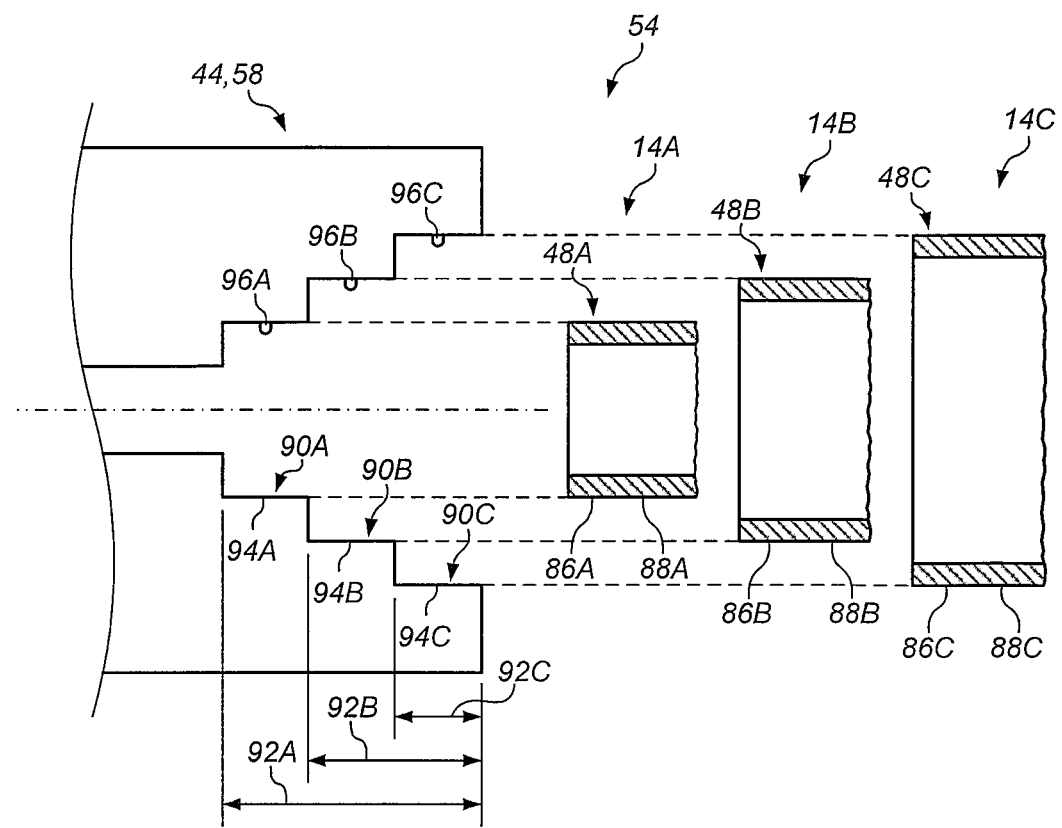
FIG. 5 is a schematic diagram of yet another keying feature in accordance with embodiments of the present technique.

FIG. 5 is a cross-sectional view that illustrate features of another embodiment of the keying feature 54 in accordance with one or more embodiments of the present technique. The illustrated embodiment includes an electromechanical keying feature. As used herein "electromechanical keying feature" refers to a keying feature that employs mechanical interfaces between a plurality of structural members in coordination with generating, transmitting, modifying, and/or receiving an electrical signal. In the illustrated embodiment, the mask-keying features 56A, 56B, and 56C include the inlets 48A, 48B, and 48C of the mask 14A, 14B, and 14C, respectively. The inlets 48A, 48B, and 48C each have different external diameters from one another. For instance, in the illustrated embodiment, the inlet 48A of the infant-sized mask 14A includes a circular conduit 86A having a first diameter 88A, the inlet 48B of the child-sized mask 14B includes a circular conduit 86B having a second diameter 88B, and the inlet 48C of the adult-sized mask 14C includes a circular conduit 86C having a third diameter 88C. The first diameter 88A is less than the second diameter 88B, and the second diameter 88B is less than the third diameter 88C. The complementary keying feature 58 of the connector 44 includes a series of concentric indentations configured to accept each of inlets 48A, 48B, and 48C. In the illustrated embodiment, a first indentation 90A includes a first depth 92A and a first diameter 94A, a second indentation 90B includes a second depth 92B and a second diameter 94B, and a third indentation 90C includes a third depth 92C and a third diameter 94C. The first depth 92A is greater than the second depth 92B, and the second depth 92B is greater than the third depth 92C. The first diameter 94A is approximately the same as the first diameter 88A of the mask-keying feature 48A, the second diameter 94B is approximately the same as the second diameter 88B of the mask-keying feature 48B, and the third diameter 94C is approximately the same as the third diameter 88C of the mask-keying feature 48C. Thus, in one embodiment, each of the conduits 86A, 86B, and 86C of the mask-keying features 48A, 48B, and 48C may extend into and fit snuggly with only one of the concentric indentations 90A, 90B, and 90C, respectively.

In one embodiment, the indentation 90A, 90B, or 90C engaged by the mask-keying feature 48A, 48B, or 48C can be assessed to determine which of the pre-selected flow parameters should be implemented. For instance, in the illustrated embodiment, each of the indentations 90A, 90B, and 90C includes a switch 96A, 96B, and 96C. When the mask 14A, 14B, or 14C is coupled to the ventilator supply system 12, the exterior of the conduit 86A, 86B, or 86C engages one of the switches 90A, 90B, and 90C, respectively. Engagement of the switch 90A, 90B, or 90C provides an indication of the desired flow parameters. In one embodiment, the switches 96A, 96B, or 96C may complete an electrical circuit and/or provide an electrical signal that is employed to automatically select the pre-determined flow parameters for the air/oxygen in a manner similar to that discussed above with regard to the electrical keying feature of FIG. 3. In another embodiment, the switches 96A, 96B, and 96C may provide a mechanical force to engage a valve or the regulator 18 to automatically select the flow parameters of the air/oxygen in a manner similar to that discussed above with regard to the mechanical keying feature of FIGS. 4A-4D.

In one embodiment, the inside diameter of the conduits 86B and 86C of the adult and child masks 14B and 14C may be approximately the same. For instance in one such embodiment, the internal diameter of the conduits 86B and 86C of the adult and child masks 14B and 14C may be approximately the same and the internal diameter of the conduit 86A of the infant mask 14A may be significantly smaller. The outside diameter 88B and 88C of the conduits 86B and 86C of the adult and child masks 14B and 14C may be different, such that each of the adult mask 14C and the child mask 14B may fit snuggly into only one of the indentations 90B and 90C. Such an embodiment may be useful as a keying feature for the adult and child ventilation process. The internal and external diameter of the conduit 86A of the infant mask 14A are both smaller than the internal and external conduits 86B and 86C of the adult and child masks 14B and 14C. This can severe as a keying feature for infant artificial respiration protocols. The small internal and external diameter of the conduit 86A of the infant mask 14A allows for low flow characteristics needed for low volume ventilation for children.

Figure 6:
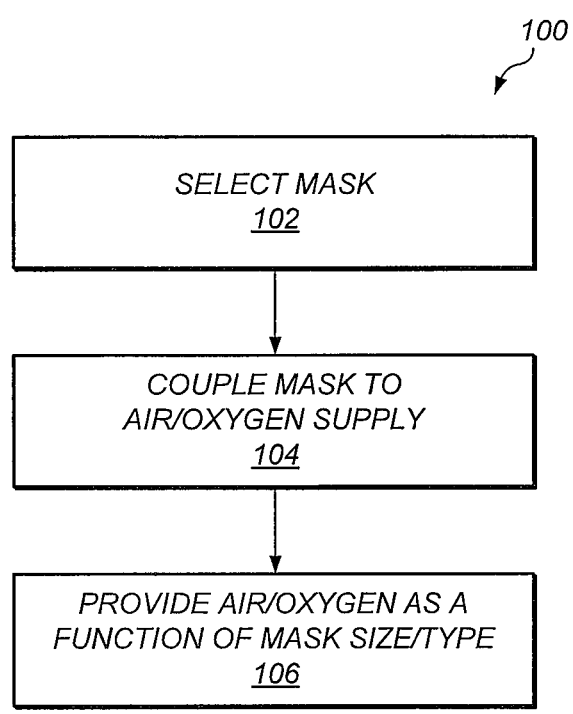
FIG. 6 is a flow chart illustrating a method of operating the air/oxygen supply system in accordance with embodiments of the present technique.

FIG. 6 is a flowchart that illustrates a method 100 of operating the ventilator system 10 in accordance with one or more embodiments of the present technique. The method 100 generally includes automatically providing air/oxygen at pre-selected flow parameters (e.g., maximum pressure limit, breath volume and respiratory-rate) as a function of characteristics (e.g., a size and/or type) of a mask 14 coupled to the air/oxygen ventilator system 10. In one embodiment, the method 100 includes selecting a mask, as depicted at block 102. Selecting a mask (block 102) may include a user selecting one mask 14 from a plurality of masks 14A, 14B, or 14C that are available for use with the ventilator system 10. For example, in one embodiment, the plurality of available masks available for use may include three masks 14A, 14B, and 14C of varying sizes. The three masks 14 may include one mask sized to fit an infant's face 14A, one mask sized to fit a child's face 14B, and one mask sized to fit an adult's face 14C. In such an embodiment, selecting the mask (block 102) may include the user assessing the size of the subject 24, estimating which mask 14A, 14B, or 14C may be of the appropriate size, holding the mask 14A, 14B, or 14C to the subject's face region 26 to ensure a proper fit, and repeating the procedure until the user determines which mask 14A, 14B, or 14C appears to provide the best fit and seal to the subject's face region 26.

In one embodiment, the method 100 also includes coupling the mask to an air/oxygen supply, as depicted at block 104. In one embodiment, this may include the user physically coupling an inlet of the mask 14 to an outlet of the ventilator supply system 12. For example, the mask 14 may be coupled directly to a connector 44 of the ventilator supply system 12 or the mask 14 may be coupled to a mask conduit 22, such as flexible tubing that extends between the inlet 48A, 48B, or 48C of the mask 14 and the outlet 40 of the ventilator supply system 12. Coupling the mask 14 to the air/oxygen supply system 12 may include engaging a mask-keying feature 56A, 56B, or 56C with a complementary keying feature 58 of the ventilator supply system 12.

As depicted at block 106, the method 100 may includes providing air/oxygen flow as a function of the mask type and/or size. For instance, in one embodiment, providing air/oxygen flow as a function of the mask type and/or size (block 106) includes assessing the size of the mask 14 that is coupled to the air/oxygen supply system 12. Assessing the size of the mask may include assessing a signal that is indicative of the mask coupled to the ventilator supply system 12 (e.g., in an embodiment including an electrical keying feature). In another embodiment (e.g., an embodiment including a mechanical keying feature) assessing the size of the mask includes configuring the ventilator supply 12 in response to a mechanical stimulus provided by coupling the mask 14 to the ventilator supply 12 (e.g., the depression of the stem engaging a valve of the ventilator supply).

Further providing air/oxygen flow as a function of the mask type and/or size (block 106) may include providing air/oxygen flow with flow parameters associated with the type/size of the mask 14 coupled to the ventilator supply 12. For example, where the regulator 18 is configured to provide air/oxygen at a pre-selected maximum pressure limit, breath volume, and/or respiratory-rate based on the size of the mask 14 coupled to the supply system 12, the air/oxygen may be routed from the ventilator system 10 in accordance with a set of flow parameters associated with the size of the mask 14.

Various elements and aspects of the method 100 described herein can be combined, reversed, or omitted. For example, with respect to providing air/oxygen as a function of mask type/size, the method may include only this step, and it not dependent on the steps of selecting a mask (block 102) and coupling the mask to the air/oxygen supply (block 104), that may be performed by a user.

It is further noted that the ventilator system 10 may be suited for configuration as a portable ventilation system 10. For instance, each of the components of the ventilation system 10 can be combined into a single-portable unit that can be stored and activated at or near the location of an emergency. Such a portable unit, may be suitable for use in homes, schools, industrial settings, hotels, commercial office buildings, commercial aircraft, and the like, where having a conveniently placed ventilator system 12 may be beneficial to providing assistance to those performing CPR.

In one embodiment, such as that depicted in FIG. 2, the cylinder 30 may include a shape conducive to being handled by a user. For example, the cylinder 30 may include a diameter, shape, grip, handle, or the like, such that a user can grasp the ventilator system 10 by the cylinder 30. Such a configuration may assist a user's dexterity in handling the ventilator system 10 before, during and after the administration of CPR to the subject 24. For example, a user may hold the ventilator system 10 and mask 14 secure to the face region 26 of the subject 24 with one hand while checking the pulse of the subject 24 with the other hand. Other embodiments may include features such as wheels or a carrying strap conducive to transport and handling of the system 10.

Further, it is anticipated that dialing a 911 operator may be helpful, thus, certain embodiments may include a telephonic device, such as a cell phone, or other communications device, that may enable a user to make a call to 911 in conjunction with use of the ventilator system 10. For example, in one embodiment, a button, voice activated, or user activated switch may be located on the ventilator system 10 such that a user may place a call to a 911 operator. In one embodiment, the ventilator system 10 may be configured to only place calls to 911, and not receive 911 calls. Accordingly, there may be no additional access fee required as connections to 911 may not be charged a fee and operation of such a uni-directional cellular may not require a monthly access fee. One embodiment may include the ventilator system 10 configured to provide for wireless internet access, satellite phone access, access to an operator, access to an emergency room physician, access to a CPR support center, or the like.

Although a portable configuration may be advantageous in certain scenarios, the ventilator system 10 may also include a generally non-portable configuration. For example, where it is anticipated that the ventilation system 10 may be used for an extended period of time (e.g., an hour or more), the source 16 may be increased in size or supplemented by another supply, such as a large cylinder, a second small cylinder, or stand-alone oxygen supply unit generally available in a hospital or similar medical facility or aircraft. Such an embodiment may be employed within a health care facility to ensure that flow parameters are selected based on the mask coupled to the ventilator system 10, and ensure that even trained professionals do not inadvertently select inappropriate flow parameters.

Although certain embodiments have been discussed in detail, other embodiment of the system 10 are within the scope of this disclosure. For example, although much of the disclosure has considered the type and/or size of a mask, other embodiments may consider the type and/or size of another air delivery device, such as an endrotracheal tube or other device configured to route air/oxygen to the lungs of a subject. Further, the system 10 has been discussed in the context of a ventilator system; however, other embodiments may include similar forms of air/oxygen delivery devices, such as a respirator.

In other embodiments, the ventilator system 10 may incorporate and/or be combined with various medical devices. For example, in one embodiment, the ventilator system 10 may be provided in conjunction with and/or include a defibrillator. As discussed above, when air/oxygen is delivered via the ventilator supply system, and is used to assist respiration and oxygenation, the defibrillator may, then, be employed in an attempt to correct lethal cardiac electrical activity. For instance, CPR may be performed prior to administering an electric shock to the heart via the defibrillator, as this will increase the likelihood of defibrillation success, and improve the chance for victim survival. The ventilator system 10 may include a carbon dioxide detector in one embodiment. For example, a carbon dioxide detector cartridge may be placed in the system and configured to detect the presence of carbon dioxide and confirm air movement from the patient. Further, embodiments may include airway devices such as oral airways, nasal trumpets, laryngeal mask airways and CPR prompts (e.g., audible bee to prompt when to do compressions), or Broslow charts. Further, embodiments may include endrotracheal tube connections having a keying feature similar to those described herein. Such embodiments may enable use of the system with endrotracheal tubes and/or masks.

The ventilator system 10 may include medications provided with the unit that could be administered to the subject 24. For example, the ventilator system 10 may include a compartment configured to contain Epinephrine for allergic reactions or asthmatic emergencies. These could be used only under stringent guidelines, and/or specific direction from an operator or a physician.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed or omitted, and certain features of the invention may be utilized independently, all as would be apparent to one skilled in the art after having the benefit of this description of the invention. Changes may be made in the elements described herein without departing from the spirit and scope of the invention as described in the following claims. The words "include", "including", and "includes" mean including, but not limited to.

What is claimed is:

1. A method, comprising:
selecting a mask from a set of two or more ventilator masks, wherein each of at least two of the ventilator masks is configured in a size that will fit upon a different range of sizes of human faces than at least one other ventilator mask in the set of two or more ventilator masks, wherein each of the at least two ventilator masks comprises a mechanical keying feature that is different from a mechanical keying feature of the other ventilator masks of the at least two ventilator masks;
coupling the selected ventilator mask to an air/oxygen supply system, wherein the an air/oxygen supply system comprises mechanical keying features that are complementary to the keying features of the ventilator masks, wherein one switch among a plurality of switches on the air/oxygen supply system is switched from one state to another when the selected ventilator mask and the air/oxygen supply system are coupled;
automatically determining the size of the ventilator mask coupled to the air/oxygen supply system based on the mechanical keying feature of the selected ventilator mask;
automatically setting, based on the size of the ventilator mask determined to be coupled to the air/oxygen supply system based on the mechanical keying feature, a pre-selected maximum pressure limit, a pre-selected breath volume, or a pre-selected respiratory-rate to provide air/oxygen to the selected ventilator mask as a function of the size of the ventilator mask coupled to the air/oxygen supply system, wherein the setting of the pre-selected maximum pressure limit, the pre-selected breath volume, or the pre-selected respiratory-rate to provide air/oxygen is based on which one of the plurality of switches is switched when the selected ventilator mask and the air/oxygen supply system are coupled, wherein which one of the plurality of switches is switched is based on the mechanical keying feature of the selected ventilator mask; and automatically providing air/oxygen to the selected ventilator mask at the pre-selected maximum pressure limit, the pre-selected breath volume, or the pre-selected respiratory-rate.

2. The method of claim 1, wherein coupling the ventilator mask to the air/oxygen supply system comprises selecting mask having a size based on a fit of the mask to a face of a human subject, and coupling the selected mask to the air/oxygen supply system.

3. The method of claim 2, wherein the selected mask, when coupled to the air/oxygen supply system, interacts with the air/oxygen supply system to thereby initiate the pre-selected maximum pressure limit, breath volume, and respiratory-rate from the air/oxygen supply system.

4. The method of claim 1, wherein the mask size comprises one of a plurality of mask sizes.

5. The method of claim 4, wherein the plurality of mask sizes comprise one or more infant-size, one or more child-size, and one or more adult-size.

6. The method of claim 1, wherein automatically providing air/oxygen at a pre-selected maximum pressure limit, breath volume and respiratory-rate, comprises providing air/oxygen at a pre-selected maximum pressure limit, breath volume and respiratory-rate for one of an infant, a child, or an adult.

7. The method of claim 6, further comprising controlling the pressure below a maximum safe pressure for a mask user's lungs.

8. The method of claim 6, further comprising providing the air/oxygen at an inspiratory time and an expiratory time as a function of the size of the mask coupled to the air/oxygen supply system.

9. The method of claim 6, further comprising providing the air/oxygen at a pre-selected frequency as a function of the size of the mask coupled to the air/oxygen supply system.

10. The method of claim 1, comprising providing a signal and/or alarm corresponding to a measurement of a current pressure of a supply of the air/oxygen the supply system.

11. The method of claim 1, comprising providing a signal and/or alarm that indicating whether or not the air/oxygen supply is functioning properly.

12. The method of claim 11, wherein providing a signal and/or alarm comprises providing a signal corresponding to a measurement of the pressure of the air/oxygen being administered.

13. A ventilator system, comprising:
a set of two or more ventilator masks, wherein each of at least two of the ventilator masks is configured in a size that will fit upon a different range of sizes of human faces than at least one other ventilator mask in the set of two or more ventilator masks, wherein each of the at least two ventilator masks comprises a mechanical keying feature that is different from a mechanical keying feature of the other ventilator masks of the at least two ventilator masks; and a ventilator supply system, comprising:
an air/oxygen source;
a connector configured to couple with each of the at least two ventilator masks; and
an air/oxygen supply system comprising mechanical keying features that are complementary to the mechanical keying features of the ventilator masks, wherein one switch among a plurality of switches on the air/oxygen supply system is configured to switch from one state to another when one of the ventilator masks and the air/oxygen supply system are coupled, wherein the air/oxygen supply system is configured to:
determine, based on the mechanical keying feature of the ventilator mask that is coupled to the connector, which of the ventilator masks from the set of ventilator masks is coupled to the connector;
automatically set, based on the mechanical keying feature of the ventilator mask determined to be coupled to the connector, a pre-selected maximum pressure limit, a pre-selected breath volume, or a pre-selected respiratory-rate to provide air/oxygen to the ventilator mask coupled to the air/oxygen supply system as a function of the size of the ventilator mask coupled to the air/oxygen supply system, wherein the setting of the pre-selected maximum pressure limit, the pre-selected breath volume, or the pre-selected respiratory-rate to provide air/oxygen is based on which one of the plurality of switches is switched when the coupled ventilator mask and the air/oxygen supply system are coupled to one another, wherein which one of the plurality of switches is switched is based on the mechanical keying feature of the coupled ventilator mask; and
regulate air/oxygen flow to provide air/oxygen to the ventilator mask coupled to the air/oxygen supply system at the pre-selected maximum pressure limit, the pre-selected breath volume, and the pre-selected respiratory-rate.

14. The ventilator system of claim 13, wherein the air/oxygen flow is regulated at a selected I:E ratio of air/oxygen.

15. The ventilator system of claim 13, further comprising a mask conduit configured to couple the ventilator supply to the coupled ventilator mask.

16. The ventilator system of claim 15, wherein the mask conduit comprises the mechanical keying feature configured to engage the complementary mechanical keying features of the ventilator supply system.

17. The ventilator system of claim 16, wherein the mechanical keying feature comprises a plurality of protrusions configured to engage one or more indentations of the complementary mechanical keying features.

18. The ventilator system of claim 13, wherein the range of sizes comprises one of an infant-size range, a child-size range, and an adult-size range.

19. The ventilator system of claim 13, comprising a signaling device configured to transmit a signal indicating that the air/oxygen supply system is in need of service.

20. The ventilator system of claim 13, comprising a signaling device configured to transmit a signal corresponding to a measure of one or more observed air/oxygen flow parameters.

21. The ventilator system of claim 13, comprising a signaling device configured to transmit a signal indicating a condition of at least one of: blockage, proper flow, and/or leakage of air/oxygen.

22. The ventilator system of claim 13, comprising a communication device configured to enable communication with one or more emergency response personnel.

23. The ventilator system of claim 13, wherein the mechanical keying feature comprises a variation, from one ventilator mask to another, in the internal and/or external diameter of a collar of the mask.

24. The ventilator system of claim 13, wherein air/oxygen flow is configured to commence upon coupling of a ventilator mask to the ventilator supply.

25. The ventilator system of claim 13, wherein at least one of the switches is associated with a particular size of ventilator mask from the set of ventilator masks, wherein the at least one switch comprises a stem that is displaced when the ventilator mask of the particular size is coupled to the air/oxygen supply system.

26. The ventilator system of claim 13, wherein a switch on the air/oxygen supply system associated with a first size of ventilator mask in the set of ventilator masks operates when the first size ventilator mask is coupled with the air/oxygen supply system, wherein a switch on the air/oxygen supply system associated with a second size of ventilator mask in the set of ventilator masks is operating when the second size ventilator mask is coupled with the air/oxygen supply system.

27. A cardiopulmonary resuscitation (CPR) kit, comprising:
a set of ventilator masks, comprising:
a ventilator mask configured to fit upon a selected range of sizes of human infant faces;
a ventilator mask configured to fit upon a selected range of sizes of human child faces; and
a ventilator mask configured to fit upon a selected range of sizes of human adult faces;
wherein each of the ventilator masks comprises a mechanical keying feature that is different from a mechanical keying feature of the other ventilator masks;
a ventilator supply system comprising:
an air/oxygen source;
a connector configured to couple with each of the ventilator masks; and
an air/oxygen supply system comprising mechanical keying features that are complementary to the mechanical keying features of the ventilator masks, wherein one switch among a plurality of switches on the air/oxygen supply system is configured to switch from one state to another when one of the ventilator masks and the air/oxygen supply system are coupled, wherein the air/oxygen supply system is configured to:
determine, based on the mechanical keying feature of the ventilator mask that is coupled to the connector, which of the ventilator masks from the set of ventilator masks is coupled to the connector;
automatically set, based on the mechanical keying feature of the ventilator mask determined to be coupled to the connector, a pre-selected maximum pressure limit, a pre-selected breath volume, or a pre-selected respiratory-rate to provide air/oxygen to the coupled ventilator mask as a function of the size of the ventilator mask coupled to the air/oxygen supply system, wherein the setting of the pre-selected maximum pressure limit, the pre-selected breath volume, or the pre-selected respiratory-rate to provide air/oxygen is based on which one of the plurality of switches is switched when the coupled ventilator mask and the air/oxygen supply system are coupled to one another, wherein which one of the plurality of switches is switched is based on the mechanical keying feature of the coupled ventilator mask; and
regulate air/oxygen flow to provide air/oxygen to the ventilator mask at the pre-selected maximum pressure limit, the pre-selected breath volume, and the pre-selected respiratory-rate.

28. The CPR kit of claim 27, further comprising a defibrillator. communication device configured to send a message to contact emergency response 29. The CPR kit of claim 27, further comprising a personnel.

30. The CPR kit of claim 27, further comprising emergency medications and/or airway control devices.

* * * * *

UNITED STATES PATENT AND TRADEMARK OFFICE
CERTIFICATE OF CORRECTION

PATENT NO. : 8,707,954 B2
APPLICATION NO. : 12/248203
DATED : April 29, 2014
INVENTOR(S) : McCarthy It is certified that error appears in the above-identified patent and that said Letters Patent is hereby corrected as shown below:

In the Claims:

Column 22, Delete Claim 28, lines 35-38 and substitute therefor --28. The CPR kit of claim 27, further comprising defibrillator.--.

Column 22, Delete Claim 29, lines 38-39 and substitute therefor --29. The CPR kit of claim 27, further comprising a communication device configured to send a message to contact emergency response personnel.--.

Signed and Sealed this
Ninth Day of September, 2014

Michelle K. Lee
*Deputy Director of the United States Patent and Trademark Office*